United States Patent [19]

Weickhardt

[11] 4,204,957

[45] May 27, 1980

[54] ARTIFICIAL KIDNEY

[75] Inventor: Ludwig Weickhardt, Bovenden, Fed. Rep. of Germany

[73] Assignee: Sartorius Membranfilter GmbH, Gottingen, Fed. Rep. of Germany

[21] Appl. No.: 738,905

[22] Filed: Nov. 4, 1976

[30] Foreign Application Priority Data

Nov. 21, 1975 [DE] Fed. Rep. of Germany ....... 2552304

[51] Int. Cl.² .................. B01D 31/00; A61M 1/03
[52] U.S. Cl. .................. 210/98; 128/214 E; 210/101; 210/143; 210/258; 210/321 B
[58] Field of Search .......... 210/259, 23 H, 23 F, 210/321 B, 98, 101, 143, 258; 128/214 E

[56] References Cited

U.S. PATENT DOCUMENTS

| 3,506,126 | 4/1970 | Serfass et al. ............ 210/259 X |
| 3,579,441 | 5/1971 | Brown ..................... 210/321 B X |
| 3,825,493 | 7/1974 | Brown et al. ............. 210/23 H |

FOREIGN PATENT DOCUMENTS 2334230 1/1975 Fed. Rep. of Germany ......... 210/23 F

OTHER PUBLICATIONS

Henderson et al., "Blood Purification by Ultrafiltration and Fluid Replacement (Diafiltration)", from *Trans. Amer. Soc. Artif. Int. Organs*, vol. XIII, 1967, pp. 216-221, 225 & 226.

*Primary Examiner*—Frank A. Spear, Jr.
*Attorney, Agent, or Firm*—Anthony J. Casella

[57] ABSTRACT

An artificial kidney comprising a filter which is disposed between an artery connection and a vein connection, a collecting means for the filtrate to be discharged from the filter, a means for providing a metered supply of substituate to the purified blood, and a measuring means including two weighing devices; a first of the weighing devices measures the weight of filtrate to be discharged, and a second of the weighing device measures the weight of the substituate; the measuring means controls the providing means whereby the metered supply of substituate is in a fixed weight proportionality to the filtrate weight.

7 Claims, 2 Drawing Figures

ARTIFICIAL KIDNEY

The invention relates to an artificial kidney which is provided with a filter disposed between the artery connection and the vein connection, with a collecting device for the filtrate which is to be discharged, and with a device for the metered supply of substitute to the purified blood.

An artificial kidney of this kind has already been described in U.S. Pat. No. 3,483,867.

The problem underlying the invention is that of so constructing the artificial kidney that the substitute can be supplied to the purified blood in a simple manner continuously and with fixed proportionality to the amount of dischargeable filtrate removed from the filter.

In an artificial kidney of the kind described above this problem is solved in the present invention by a measuring system comprising two weighing devices, one of which measures the weight of the amount of filtrate to be discharged, while the substitute is given up in fixed weight proportionality by way of the other weighing device.

A metering system for peritoneal dialysis is already known (DT-AS 2,101,168). In this metering system, the volumes of the incoming and outgoing cleansing solution are compared with one another by mutual displacement, the amount of liquid withdrawn being received in a measuring vessel, and the state of filling of flexible metering bags being used to control the pumps. In connection with a system of this kind, it is pointed out that weight measurement could be effected substantially more easily, but entails the disadvantage that in the event of a change of the composition of the cleansing solution computational corrections would have to be made, taking into account the specific gravity of the solution. For this reason volumetric measurement is preferred.

Weight measurement has hitherto been regarded as disadvantageous. The artificial kidney of the invention has, however, the advantage that it utilises the desirable features of weight measurement, and at the same time avoids the detrimental properties with the aid of two weighing devices and of a measuring system to which fixed desired values can be fed and which continuously controls the supply of substituate in an artificial kidney in which the filtrate is discharged.

Between a first measuring vessel associated with the first weighing device and a filter connection for the filtrate which is to be discharged a first pump is disposed. If this pump is in the form of a vacuum pump, it is ensured that in the event of damage to the filter membrane during operation the pump will be stopped by means of a signal from a blood detector downstream of the pump and that only the space between the pump and the filter will be filled with the patient's blood before the process is interrupted. An excessive discharge of blood from the patient is thus prevented.

Furthermore, a second pump is expediently disposed between a second measuring vessel associated with a second weighing device and a connection to the pipe carrying purified blood.

It is advantageous for the measuring system to contain a device for forming the quotient of the weight of the first measuring vessel and that of the second measuring vessel, this device being followed by a device for comparing the quotient with at least one desired value and operating the second pump in dependence on the result of the comparison, so that proportionality between the amount of filtrate discharged and the amount of substitute supplied is maintained.

The measuring system may, in addition, contain a device which operates the first pump in dependence on the result of the comparison between the filter power measured by the first weighing device and upper and lower tolerance limits. It is thereby ensured that a determined filter power is maintained.

Finally, the measuring system may contain a device which compares the stipulated desired amount of substituate with the actual amount substituted and terminates the diafiltration when equality is achieved.

The invention is explained more fully by way of example with the aid of the accompanying drawings.

Figure 1:
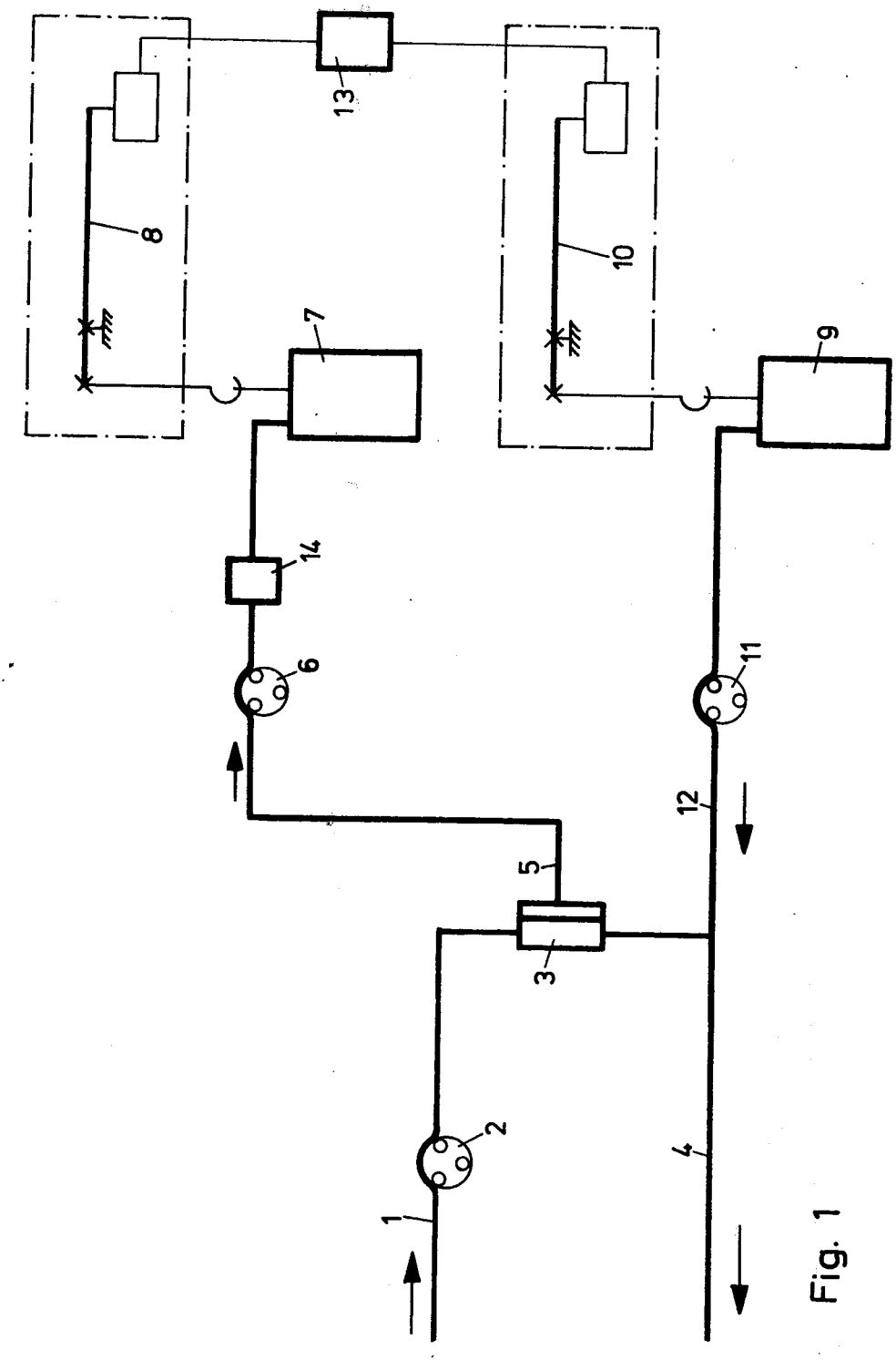
FIG. 1 shows diagrammatically one form of construction of an artificial kidney.

In a hose 1 the arterial blood is supplied by means of a hose pump 2 to the filter 3, from which the purified blood is fed on the vein side by way of the hose 4. From the filter 3 a hose 5 carries the filtrate which is to be discharged by way of a hose pump 6 and a blood detector 14 to a first measuring vessel 7, with which a first weighing device 8 is associated. The first pump 6 maintains a reduced pressure in the portion of the piping as far as the filter 3.

A second measuring vessel 9, with which a second weighing device 10 is associated, is connected by way of another hose pump 11 and a hose 12 to the hose 4 for the return of the purified blood.

The weighing device 8 and the weighing device 10 are coupled to one another by way of a diagrammatically indicated measuring system 13 in such a manner that in dependence on the weight of the amount of filtrate supplied to the measuring vessel 7 substitute, in a proportion which is fixed in relation to the amount of filtrate withdrawn, is supplied from the second measuring vessel 9 to the purified bloodstream by way of the hose pump 11 and the pipe 12.

Figure 2:
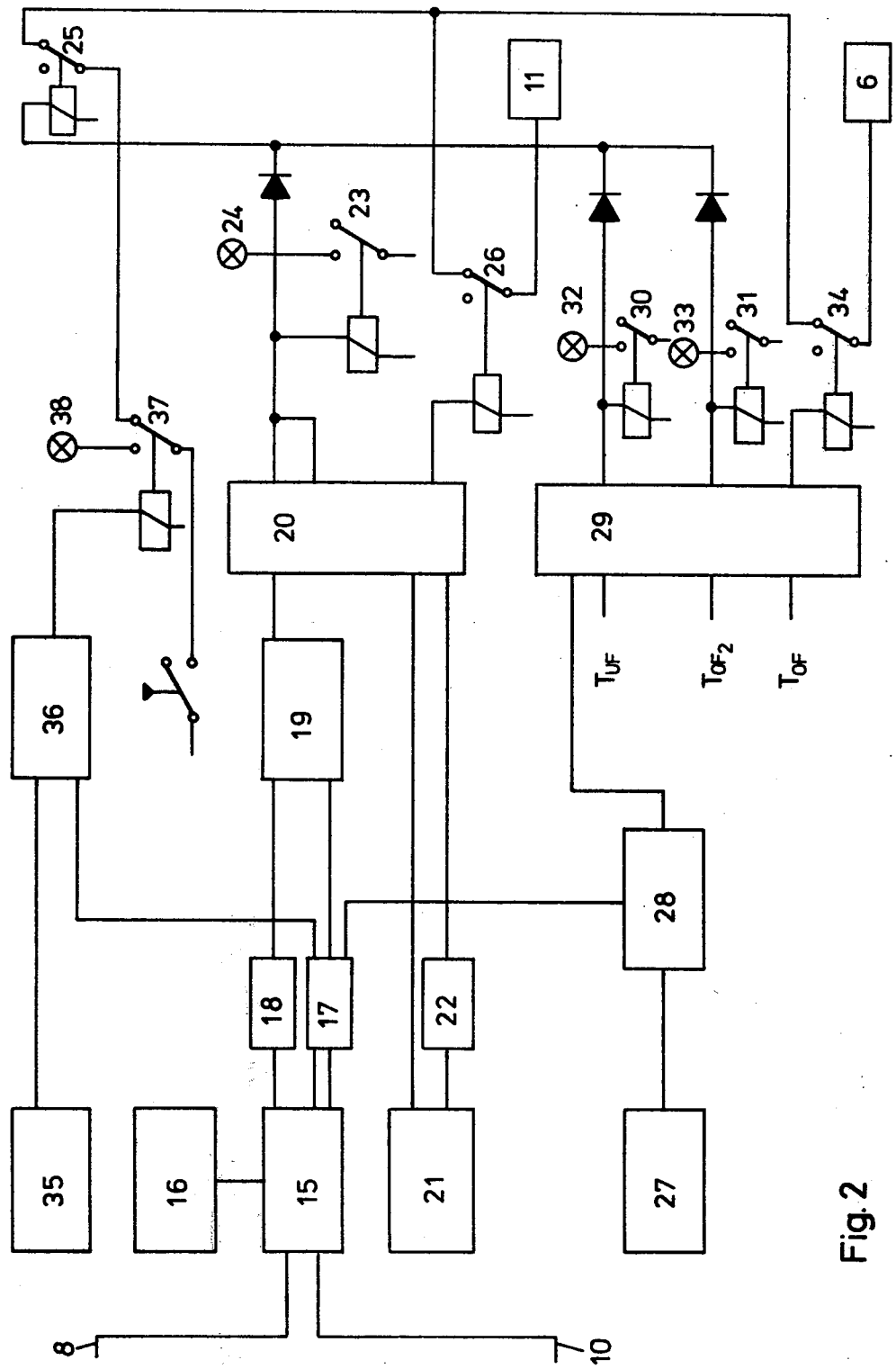
FIG. 2 shows a form of construction of the measuring system of FIG. 1.

As can be seen in FIG. 2, the weight of the amount of filtrate, measured by the weighing device 8, and the weight of the amount of substituate, weighed by the weighing device 10, are transmitted to respective stores 17 and 18 by a measuring point selector 15 and a digital voltmeter 16.

The value of the amount of substituent and the value of the amount of filtrate are passed to a quotient former 19 and the quotient (quotient=filtrate weight/substituate weight) is calculated. In a comparator 20, the quotient obtained on each occasion is compared with fixed values, or else with values which have been selected by the doctor via an input unit 21.

The following values are preferably compared:
quotient Q with a value 0.98
quotient Q with a desired value
quotient Q with a desired value x factor.

The desired value is fed in by way of an input unit 21 and multiplied by the factor in a multiplier 22. The product of desired value x factor and the desired value are compared in a comparator 20 with the respective quotient. If the quotient is lower than 0.98 or higher than the product of desired value x factor, a perceptible signal 24 is given by a switch 23 and the pumps 6 and 11 are switched off by a switch 25. If the quotient is equal to or lower than the desired value, the pump 11 is switched off by a switch 26.

In addition, the filter power is determined by the measuring system 13. For this purpose the value of the amount of substituate is transmitted from store 17 and the time from a unit 27 to a computer 28, and the weight variation per time $\Delta G/t$ is determined.

This value $\Delta G/t$ is transmitted to a comparator 29 and compared with fixed tolerance limits—in this case with a lower tolerance limit of filter power $T_{UF}$, with a first upper tolerance limit of the filter power $T_{OF}$, and with a second upper tolerance limit $T_{OF_2}$.

If $\Delta G/T < T_{UF}$ or $> T_{OF_2}$, perceptible signals 32 and 33 are given by means of switches 30 and 31 and the pumps 6 and 11 are switched off. If $\Delta G/t > T_{OF}$, the pump 6 is switched off by a switch 34.

Finally, a predetermined desired amount of substituate 35 is compared in a comparator 36 with the value of the actually substituted amount from the store 17, and in the event of equality the dia-filtration is terminated by means of a switch 37.

A perceptible signal 38 indicates termination of the diafiltration.

I claim:

1. An artificial kidney comprising a filter disposed between an artery connection and a vein connection, a collecting means for the filtrate to be discharged from said filter, a means for providing a metered supply of substituate to the purified blood, and a measuring means including two weighing devices, a first weighing device measuring the weight of the filtrate to be discharged, and a second weighing device measuring the weight of the substituate, said measuring means further including a means for forming a quotient of the weight recorded by the first weighing device and that recorded by the second weighing device, and a comparison means for comparing said quotient with at least one desired value, said measuring means controlling said providing means in dependence on the result of the comparison whereby the metered supply of substituate is in a fixed weight proportionability to the filtrate weight.

2. An artificial kidney as claimed in claim 1, wherein a first pump means is disposed between a first measuring vessel associated with said first weighing device and a filter connection for the filtrate to be discharged.

3. An artificial kidney as claimed in claim 2, wherein said pump means is a vacuum pump.

4. An artificial kidney as claimed in claim 2, wherein the measuring means includes means for operating the first pump means in dependence on the result of a comparison between the filter power, measured by means of the first weighing device, and upper and lower tolerance limits.

5. An artificial kidney as claimed in claim 1, wherein a second pump means is disposed between a second measuring vessel associated with said second weighing device and said artery connection.

6. An artificial kidney as claimed in claim 1, wherein the measuring means includes means for terminating the dia-filtration in dependence on the result of a comparison between the weight of a predetermined amount of substituate and the weight of substituate recorded by the second weighing means.

7. An artificial kidney comprising a filter disposed between an artery connection and a vein connection, a means for collecting filtrate to be discharged from the filter, a first weighing means for weighing said collected filtrate, a means for providing a metered supply of substituate to the purified blood, a second weighing means for weighing substituate, means for comparing the weights recorded by said first and second weighing means, said comparing means including means for providing the quotient of said recorded weights and for comparing said quotient to one or more predetermined values, and said comparison means controlling said providing means in dependence on said comparison to provide substituate to the purified blood in a fixed weight proportionality to the collected filtrate weight.

* * * * *